(12) United States Patent
Chen et al.

(10) Patent No.: US 8,096,949 B2
(45) Date of Patent: Jan. 17, 2012

(54) USER INTERFACE FOR ULTRASOUND MAMMOGRAPHIC IMAGING

(75) Inventors: Jiayu Chen, Palo Alto, CA (US); Thomas P. Neff, Newark, CA (US)

(73) Assignee: U-Systems, Inc., Sunnyvale, CA (US)

( * ) Notice: Subject to any disclaimer, the term of this patent is extended or adjusted under 35 U.S.C. 154(b) by 564 days.

(21) Appl. No.: 12/167,017

(22) Filed: Jul. 2, 2008

(65) Prior Publication Data

US 2010/0004539 A1 Jan. 7, 2010

(51) Int. Cl.
*A61B 8/00* (2006.01)
(52) U.S. Cl. .................................. 600/443; 128/915
(58) Field of Classification Search ............... 600/437, 600/443–447, 459; 128/915; 345/205, 206, 345/903, 905; 378/37
See application file for complete search history.

(56) References Cited

U.S. PATENT DOCUMENTS

| | | | |
|---|---|---|---|
| 6,459,925 B1 * | 10/2002 | Nields et al. | 600/427 |
| 6,468,212 B1 | 10/2002 | Scott et al. | |
| 6,669,633 B2 * | 12/2003 | Brodsky et al. | 600/437 |
| 2007/0276250 A1 | 11/2007 | Donaldson | |
| 2008/0119731 A1 * | 5/2008 | Becerra et al. | 600/437 |
| 2009/0076385 A1 * | 3/2009 | Jackson et al. | 600/437 |

OTHER PUBLICATIONS

Hyperion Brochure.
Hyperion Ultrasound System webpage www.ultra-soundimaging.com.
Quantel Medical Webpage "Alviso B" Website/AVISO A-B.html.
Sonix CEP Product Sheet.
Sonix OP Product Sheet.

* cited by examiner

*Primary Examiner* — Francis Jaworski
(74) *Attorney, Agent, or Firm* — Cooper & Dunham, LLP (57) ABSTRACT

Methods and related apparatuses are described for acquiring and displaying ultrasound mammographic image information. The system includes an ultrasound image acquisition device having at least one ultrasonic transducer positionable by a user on breast tissue of a patient so as to provide sonographic information of the breast tissue. A processing system controls the ultrasonic transducer, receives sonographic data from the transducer, and processes the data to generate sonographic image information for real time viewing by the user. A graphical user interface includes a touch-sensitive display programmed and configured to accept user adjustments with respect to the sonographic imaging process, and display the sonographic image information to the user responsive to the accepted adjustments in real time.

26 Claims, 10 Drawing Sheets

USER INTERFACE FOR ULTRASOUND MAMMOGRAPHIC IMAGING

FIELD

This patent specification relates to ultrasonic mammographic imaging. More particularly, this patent specification relates to user interfaces for ultrasound mammographic imaging systems.

BACKGROUND

Volumetric ultrasound scanning of the breast has been proposed as a complementary modality for breast cancer screening as described, for example, in the commonly assigned US 2003/007598A1 published Jan. 9, 2003, which is incorporated by reference herein. The commonly assigned WO 2004/030523A2 published Apr. 15, 2004, which is incorporated by reference herein, describes a full-field breast ultrasound (FFBU) scanning apparatus that compresses a breast along planes such as the craniocaudal (CC) plane, the mediolateral oblique (MLO) plane, etc., and ultrasonically scans the breast. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast.

When scanning the breast tissue to make the mammographic ultrasound image, a sonographer typically positions a probe or pod containing one or more probes against the breast tissue. The sonographer also enters data using a conventional keyboard, and views images and other information on a display. Thus, during the imaging process, the sonographer is forced to split his or her attention between three main areas: the probe positioning on the tissue, the keyboard or other input devices such as sliders and knobs, and the display. Adding to the difficulty, the office or other room where the imaging is often performed is typically maintained quite dark during imaging, in order to enhance the viewing of the display.

Thus, it would be desirable to facilitate ultrasound imaging by creating a user interface that is more ergonomic and efficient for the sonographer.

SUMMARY

According to embodiments, a system is provided for acquiring and displaying ultrasound mammographic image information. The system includes an ultrasound image acquisition device having at least one ultrasonic transducer positionable by a user on breast tissue of a patient so as to provide sonographic information of the breast tissue. A processing system is provided for controlling the ultrasonic transducer, receiving sonographic data from the transducer, and processing the data to generate sonographic image information for real time viewing by the user. A graphical user interface includes a touch-sensitive display programmed and configured to accept user adjustments with respect to the sonographic imaging process, and display the sonographic image information to the user responsive to the accepted adjustments in real time.

According to further embodiments, a method is provided for acquiring and displaying ultrasound mammographic image information. The method includes positioning an ultrasonic transducer unit on the breast tissue of a patent; acquiring sonographic information of the breast tissue from the transducer unit; processing the sonographic information for real time viewing by a user; accepting user adjustments with respect to the sonographic imaging process on a touch sensitive display; and displaying the processed sonographic information on the touch-sensitive display responsive to the accepted user adjustments.

DETAILED DESCRIPTION

Figure 1:
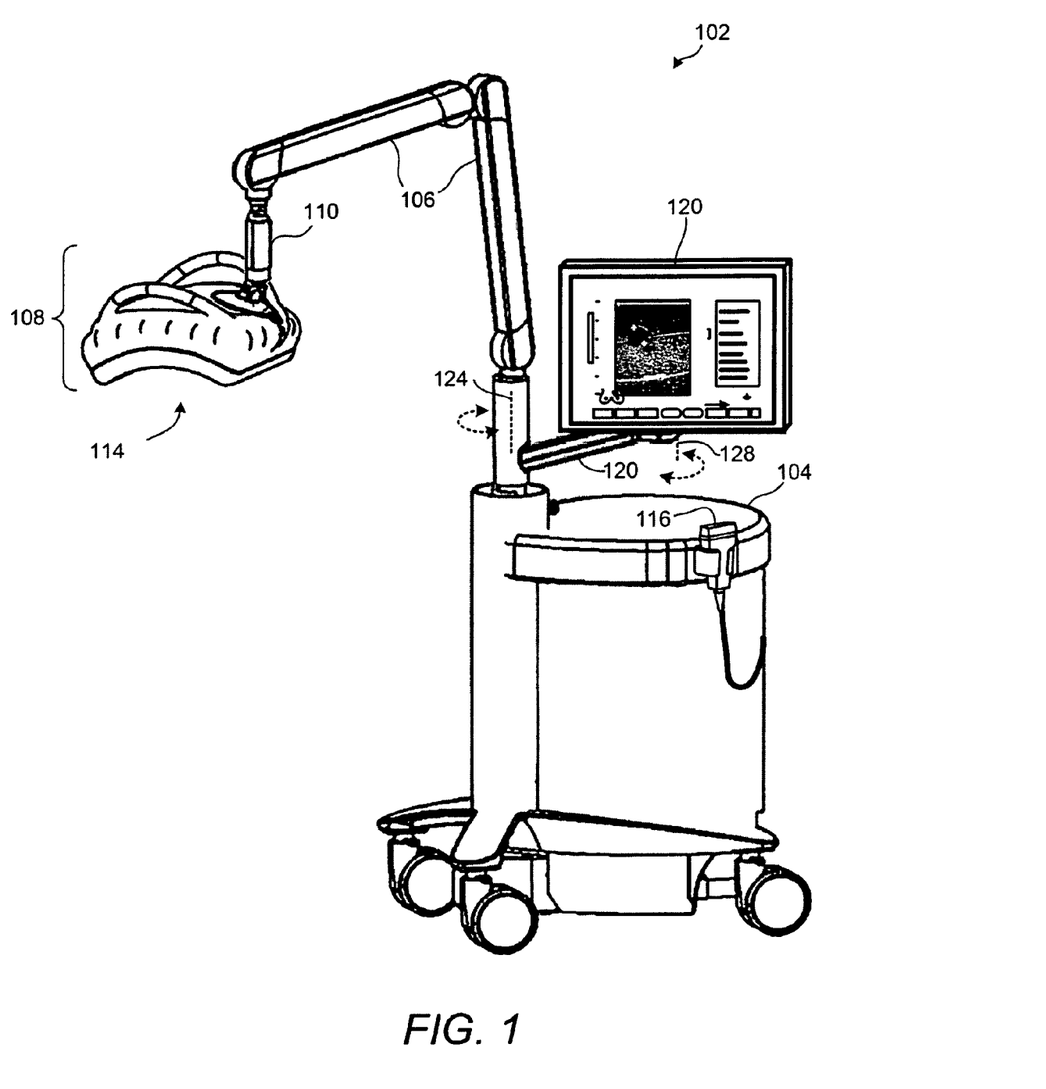
FIG. 1 illustrates a perspective view of a breast ultrasound scanning apparatus according to embodiments.

FIG. 1 illustrates a perspective view of a breast ultrasound scanning apparatus 102 according to embodiments, comprising a frame 104 that may contain an ultrasound processor including beamforming electronics, and other processors and electronics including user interface devices and processors, data management and control, and power supplies, a movable support arm 106, a automated compression/scanning assembly 108 connected to the support arm 106 via a ball-and-socket connector 110, and a monitor 111 connected to the frame 104 as shown. The housing of compression scanning assembly 108 supports a membranous sheet 114 that is disposed across a bottom opening thereof and that compresses the breast, usually toward the rib cage. An ultrasound transducer inside the housing is swept across the top of the membranous sheet 114 in a generally arcuate trajectory to ultrasonically scan the compressed breast therethrough. A top surface of the compression/scanning assembly 108 is preferably translucent to visible light to allow the user to see therethrough and onto the top of the membranous sheet 114, for facilitating ease of positioning. For embodiments in which the membranous sheet 114 is also translucent to visible light, the skin of the compressed breast can itself be seen through the top surface.

The breast of a patient (not shown) is ultrasonically scanned by a scanning apparatus 102 while the patient is in a prone position using automatic scanning assembly 108. Alternatively, the patient's breast tissue can be scanned with the patient in different positions such as an upright position or a supine position.

Breast scans are obtained under the control of a scanning engine and workstation 104. During or after the scanning process, the ultrasound scan data is provided across a computer network to an ultrasound server that processes and generates display information according to the functionalities described herein. The ultrasound server may perform other HIS/RIS (hospital information system/radiology information system) activities such as archiving, scheduling, etc. It is to be appreciated that the processing of the ultrasound scan data may be performed by any of a variety of different computing devices coupled to the computer network in various combinations without departing from the scope of the preferred embodiments.

In addition or in alternative to the compression and scanning assembly 108, tissue imaging can be obtained using a handheld ultrasonic scanning transducer 116. For further detail on ultrasonic scanning apparatuses, see e.g. International Patent Application Publication Nos. WO2008/039389 A1, WO 2007/014292 A2, and WO 05/104729 A2, each of which is incorporated by reference herein.

According to embodiments, a touchscreen user interface 120 is provided that displays images and information to and accepts input and control information from a clinician. As used herein, the term "clinician" generically refers to a medical professional, such as a radiologist, sonographer, or other person that analyzes and/or obtains medical images and/or makes clinical determinations therefrom, it being understood that such person might be titled differently, or might have varying qualifications, depending on the country or locality of their particular medical environment. As used herein, the terms radiologist and physician are used interchangeably and generically to refer to medical professionals that analyze medical images and make clinical determinations therefrom, and/or that perform medical procedures under the at least partial guidance of medical imaging systems, it being understood that such person might be titled differently, or might have differing qualifications, depending on the country or locality of their particular medical environment.

Touchscreen user interface 120 can also include conventional user input devices such as a keyboard, mouse and/or other pointing device (not shown). Touchscreen user interface 120 includes a high resolution display for displaying images and providing interactive feedback to the clinician. Alternatively, interface 120 can consist of multiple displays, with one or more having touch screen capability.

Touchscreen user interface 120 is moveably mounted on or supported by a support arm 122 that allows both rotation about a local axis 128 and a central axis 124. In this way, the clinician can position the interface 120 in a location that is convenient and ergonomically efficient for controlling and viewing the scanning process.

Figure 2:
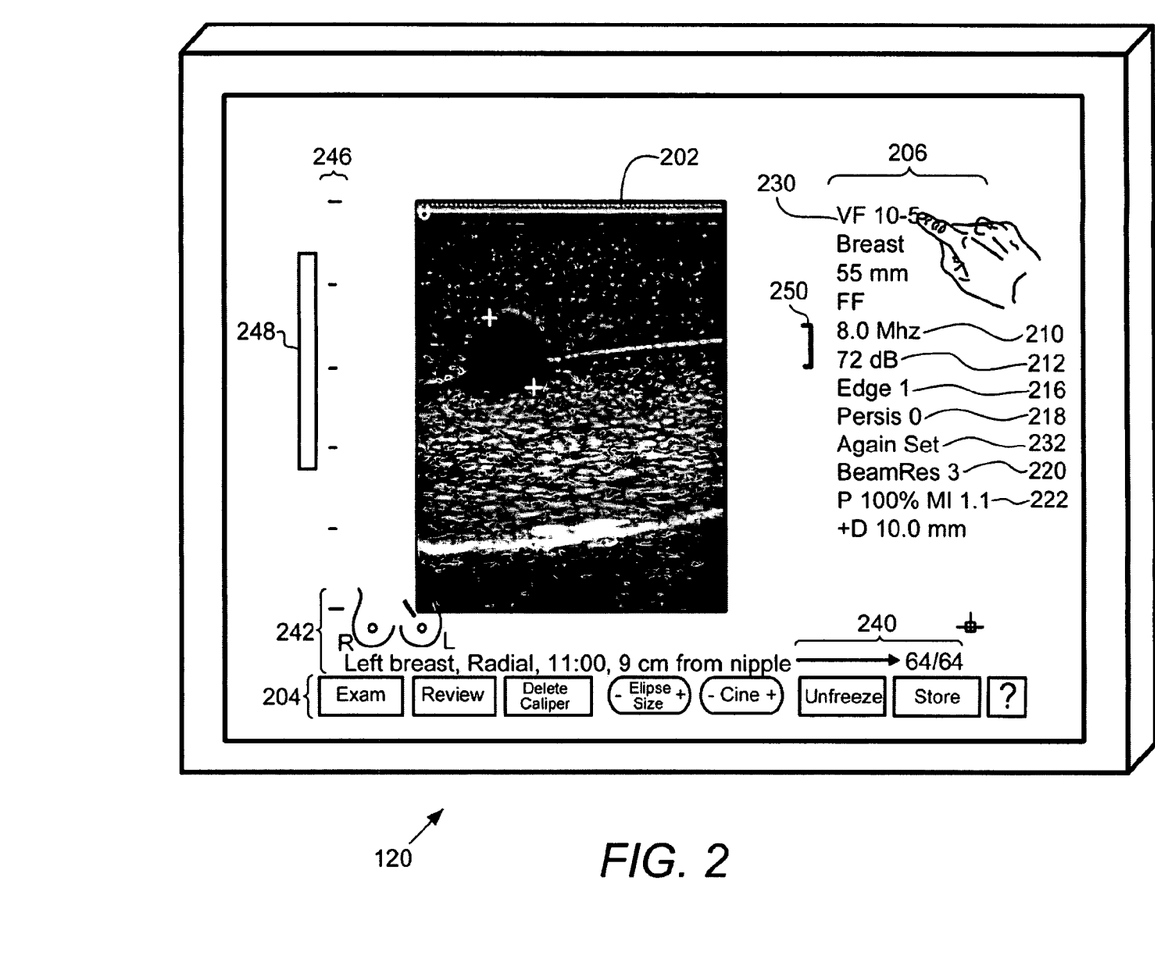
FIG. 2 shows further detail of touchscreen user interface 120, according to embodiments.

FIG. 2 shows further detail of touchscreen user interface 120, according to embodiments. Interface 120 includes an image area 202 for displaying high resolution image data real time to the clinician. As described more fully below, image area 202 can also be used to accept user input and control such as automatic image enhancement, annotations, and/or caliper measurements. Touchable menu areas 204 and 206 provide a combined status and control functionality for a set of parameters that control acquisition, processing, storage, and/or display of the ultrasound image data, such that the user can advantageously view and control these parameters without needing to look away from the touchscreen to turn a knob on a console or press a keyboard button. Touchable menu bar area 204 is used to accept various user input such as freezing and unfreezing the displayed images, processing and storing data and/or images, caliper controls, cine controls, and probe position controls. Touchable menu area 206 includes a first subset or parameters that can each be slidably adjusted in-situ at their displayed location using a touch-and-drag technique.

Such touch-and-drag slidably adjustable parameters include probe frequency 210, gain 212, dynamic range 214, degree of edge enhancement 216, degree of persistence 218, beam resolution 220, and transducer power 222, According to embodiments, the ultrasound image display is updated in real time as the slidable adjustment is being made so that the effects of that adjustment are immediately apparent to the user. Menu area 206 also includes second subset of parameters that can be tappably adjusted at their displayed location. Such tappably adjustable parameters include: probe selection 230 for switching between handheld and automated probe modes and auto-gain on/off control 232.

Cine frame slider area 240 is used to control the display of cine frames as will be described in further detail below. Probe position area 242 is used to graphically display and accept user input for information relating to the probe position, as will be described in further detail below. Depth ruler area 246 includes markers that indicate the depth in centimeters associated with the image being displayed in area 202. As will be described in further detail below, the rule makings in ruler area 246 can be used to make adjustments in depth of tissue being imaged. A contrast bar 248 is provided to help ensure a suitable contrast level for the monitor is used for the particular viewing conditions. A focal depth indicator 250 provides an indication of the focal depth setting for the imaging process. As will be described in further detail below, focal depth indicator 250 can also be used to accept user input with respect to the position and size of the focal depth range.

According to embodiments, one-touch optimization capability is provided wherein, responsive to a single tap anywhere on the displayed image area 202, automated image processing is performed to automatically select optimal parameter values for best image viewing, such as optimal dynamic range, optical degree of edge enhancement, etc., and the displayed ultrasound image is instantly displayed for the optimal parameter values. Various methods can be used to distinguish between the user's desire to perform such automated image processing from other actions such as inserting annotations and/or caliper measurement locations. For example a single tap on a live image can be used for automated image processing, a touch and drag can be used for caliper placement, and a single tap on a frozen image can be used to add annotations.

Figure 3:
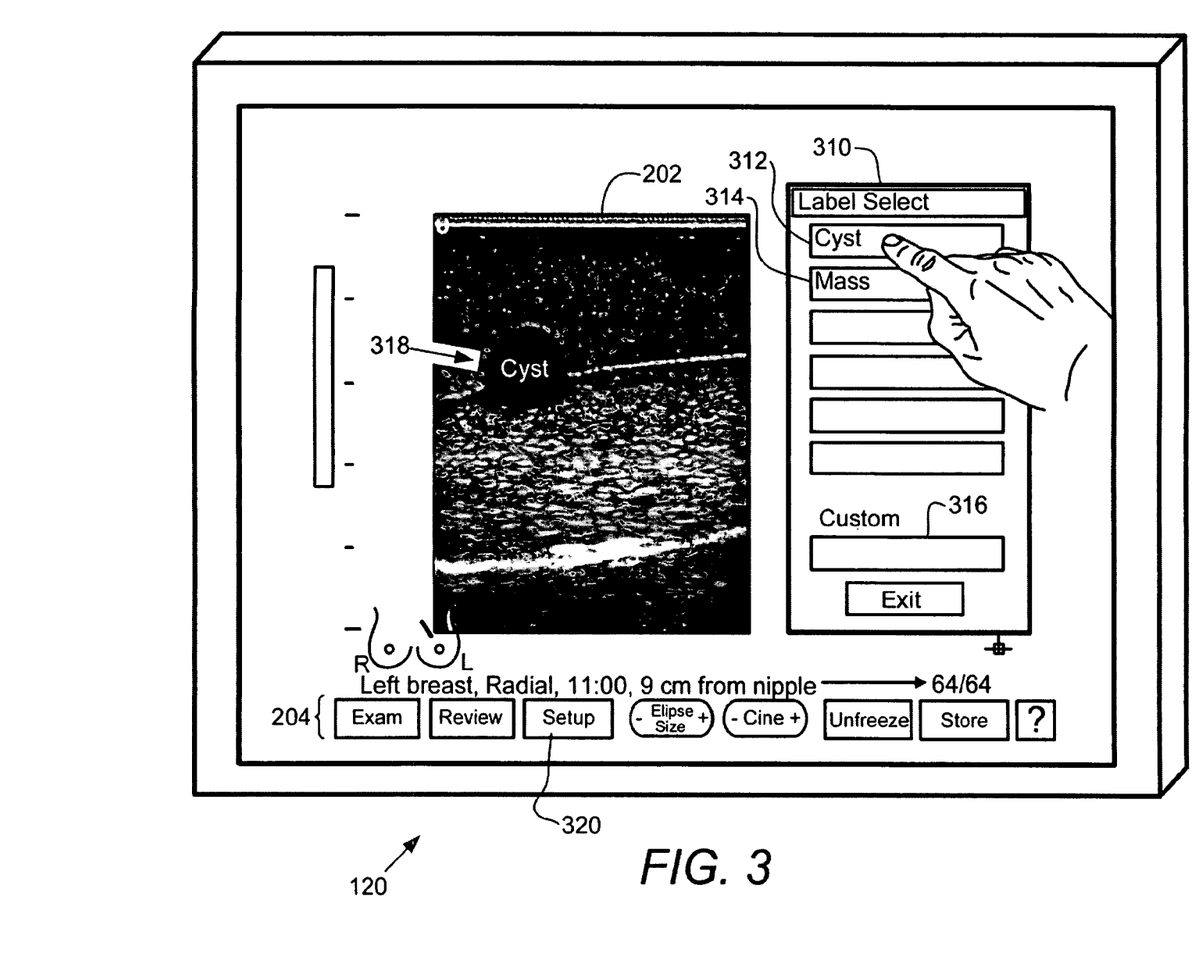
FIG. 3 illustrates a user interface screen used to generate annotations, according to embodiments.

FIG. 3 illustrates a user interface screen used to generate annotations, according to embodiments. User interface 120 is shown with an annotation label selection window 310 superimposed. The window 310 can be displayed to the user in response to, for example, a single tap on the image area 202 at the location where the annotation is desired. Label selection window 310 allows the user to select from several choices for annotations. For example, Cyst button 312 or Mass button 314 could be selected by tapping. In this example, the Cyst annotation is selected and in response a Cyst label 318 is placed at the location that the user tapped on area 202 to initiate the labeling process. Note that after the label is placed on area 202, window 310 preferably disappears. The user can then reposition any of the labels for example by a touch-and-drag operation on the label.

Window 310 also allows the user to enter a custom label in area 316. Preferably, a touch sensitive keyboard is displayed to allow the user to enter textual information. Alternatively, an external input device, such as a keyboard, could be provided. The label functionality can be setup by the user by tapping on a setup button 320 of menu area 204. Such set up could include, for example entering and/or reordering the preset annotations for window 310. According to another embodiment a generic cursor can be touch-and-dragged to a particular location of interest, and then an onscreen keyboard overlay can be spawned (for example, by a double-tap, or an onscreen "annotation" command button, etc.) to allow the user to enter annotation text for that location.

Figure 4A:
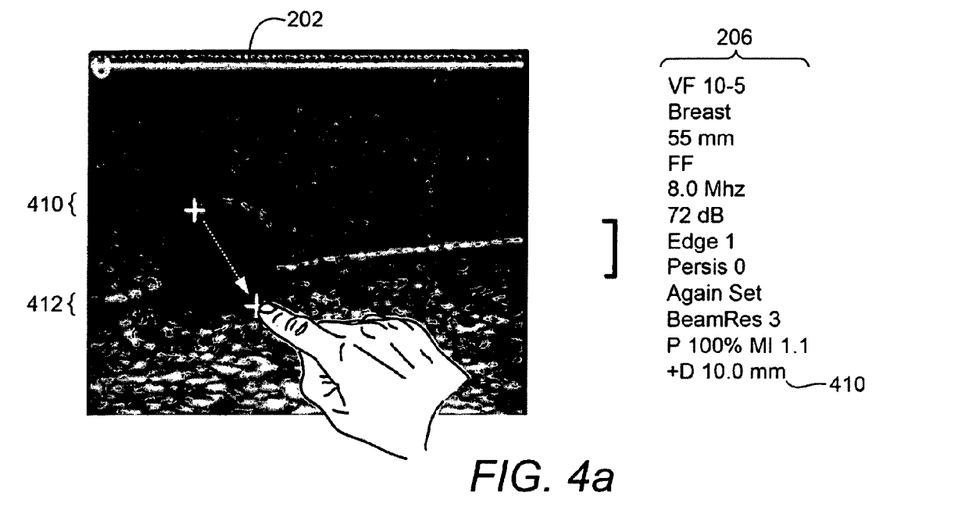
FIGS. 4a and 4b illustrate further detail for generating caliper measurements, according to embodiments.
Figure 4B:
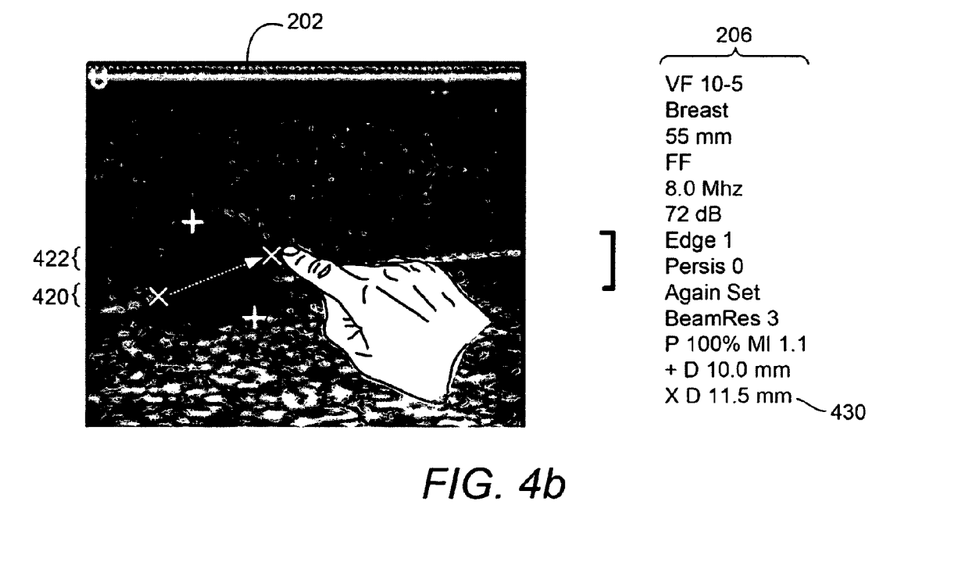

FIGS. 4a and 4b illustrate further detail for generating caliper measurements, according to embodiments. As described above, the touchscreen user interface provides the ability for the user to touch-and-drag onscreen caliper positions. In FIG. 4a, a user initiates an onscreen caliper measurement by touching at initial position 410 marked by a plus symbol, and then dragging the finger to the final position 412 in the direction shown by the white broken arrow. At final position 412 the user lifts his or her finger. In response to the described touch-and-drag technique, plus symbols are displayed in locations 410 and 412, and the measurement is calculated and displayed on line 410 in menu area 206.

In FIG. 4b, the user initiated a second onscreen caliper measurement by touching at initial position 420 marked by an X symbol, and then dragging his or her finger to the final position 422 in the direction shown by the white broken arrow. At final position 422 the user lifts his or her finger. In response to the described touch-and-drag technique, X symbols are displayed in locations 420 and 422, and the measurement is calculated and displayed on line 430 in menu area 206.

Figure 5A:
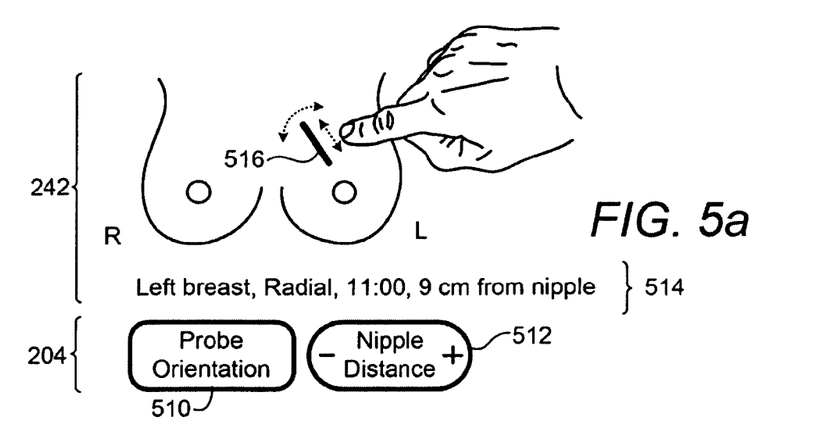
FIGS. 5a-5c illustrate further detail of a probe position area as part of a user interface, according to embodiments.
Figure 5B:
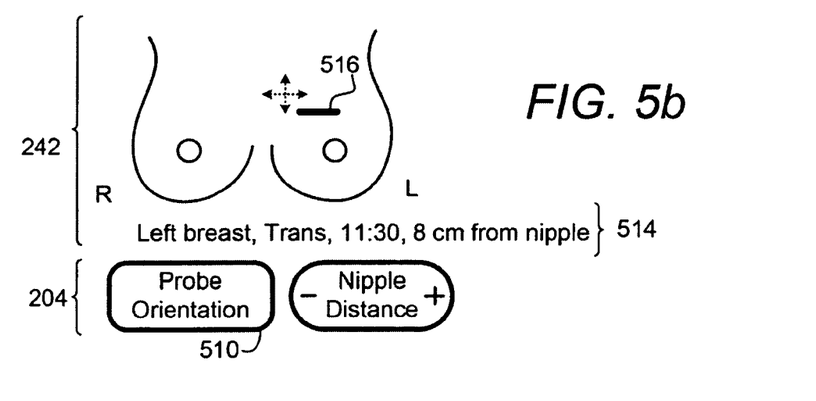
Figure 5C:
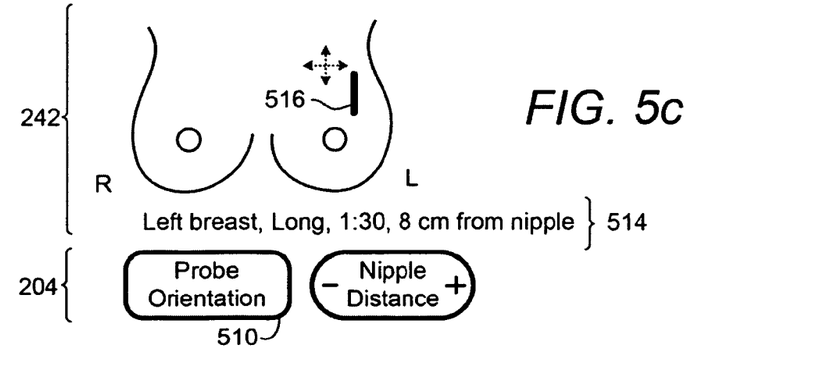

FIGS. 5a-5c illustrate further detail of a probe position area as part of a user interface, according to embodiments. For image storage purposes, the user interface includes a probe position area 242. Area 242 includes, in iconic form a conceptual outline of the breasts and nipple locations thereon. A probe position marker 516 indicated the presumed current position of a handheld probe. The user initiates the probe placement by tapping area 242. In response the icon area magnifies so as to facilitate accurate input of the placement information. The position of marker 516 can be adjusted by the user via a tough-and-drag technique in the directions shown by the broken arrows. Alternately, the position of the probe marker can be adjusted by the user single tapping the desired position within the breast outline. Text area 514 shows information that is automatically updated when adjustments are made relating to the marker position such as: left or right breast, clock position of the marker with respect to the nipple, and distance from the probe to the nipple. Also shown in area 514 is the current orientation type of the probe. In FIG. 5a, the probe orientation type is "radial." The orientation type can be selected by the user via a probe orientation button 510 in menu area 204. The user toggles through the various probe orientation types by tapping button 510. In FIG. 5b, the probe orientation type is transverse, while in FIG. 5c, the probe orientation type is longitudinal. Note that other orientation types such as anti-radial can also be included although not shown. Nipple distance button 512 provides a method of the user inputting the probe to nipple distance to compensate for different breast sizes after the probe marker is placed in the correct relative position within the breast marker.

Figure 6A:
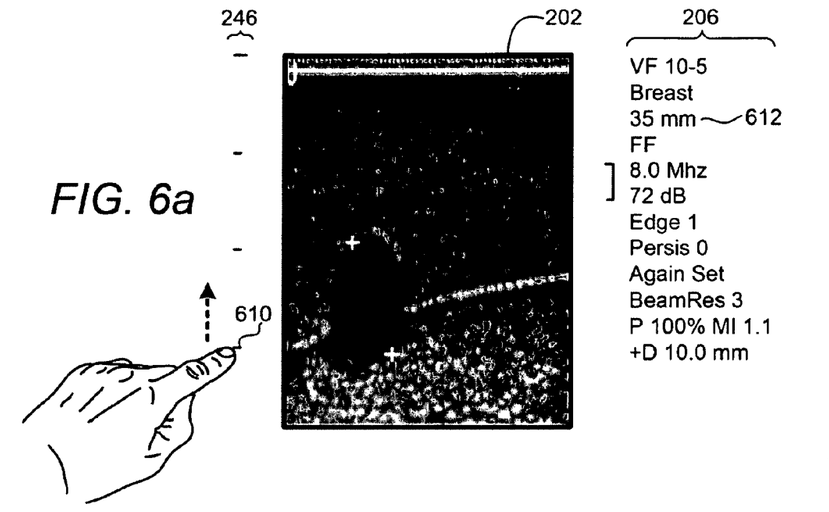
FIGS. 6a and 6b illustrate further detail of depth adjustment functionality as part of a user interface, according to embodiments.
Figure 6B:
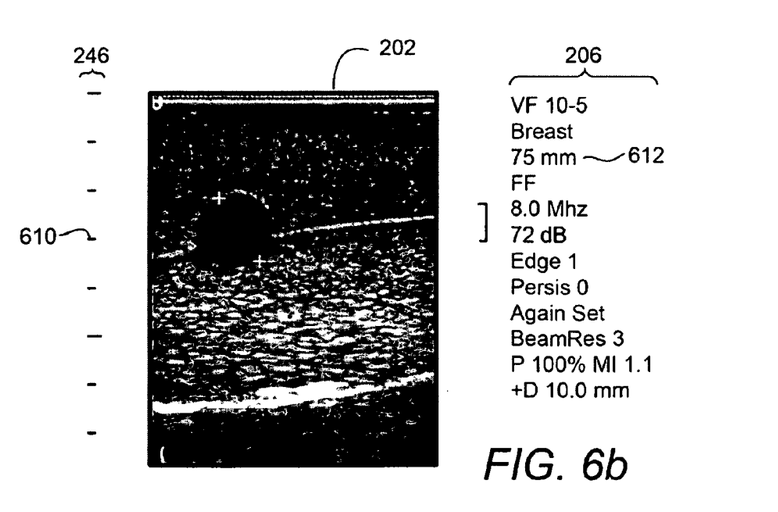

FIGS. 6a and 6b illustrate further detail of depth adjustment functionality as part of a user interface, according to embodiments. As described above, the user interface includes a depth ruler area 246. In FIG. 6a, ruler area 246 is shown with four equally spaced rule markings the spacing of which corresponds to 1 cm depth in image area 202 between each adjacent pair of markings. The total depth of the image area 202 is calculated and displayed in line 612 of menu area 206. The depth can be easily adjusted by the user by touch-and-dragging one of the rule markings. In FIG. 6a, the rule marking 610 is touched and dragged in the direction as indicated by the broken arrow. In response to the user's touch and drag operation, the displayed rule markings become compacted (i.e. the depth markers move closer together), the investigation depth of the probe is adjusted in real time, and the new image is displayed in image area 202. FIG. 6b shows the result of compacting the rule markers such that the depth is increased from 35 mm to 75 mm. (Note that the calipers are not displayed when the image is live, which is the only time that depth adjustment is supported) Note that instead of compacting the rule markings, the user could expand the markings (i.e. the depth markers moved farther apart) which would cause a corresponding decrease of the probe depth and image displayed. Alternatively, a single tap on the depth ruler could be used to set the probe depth to the depth associated with the tapped point.

Figure 7A:
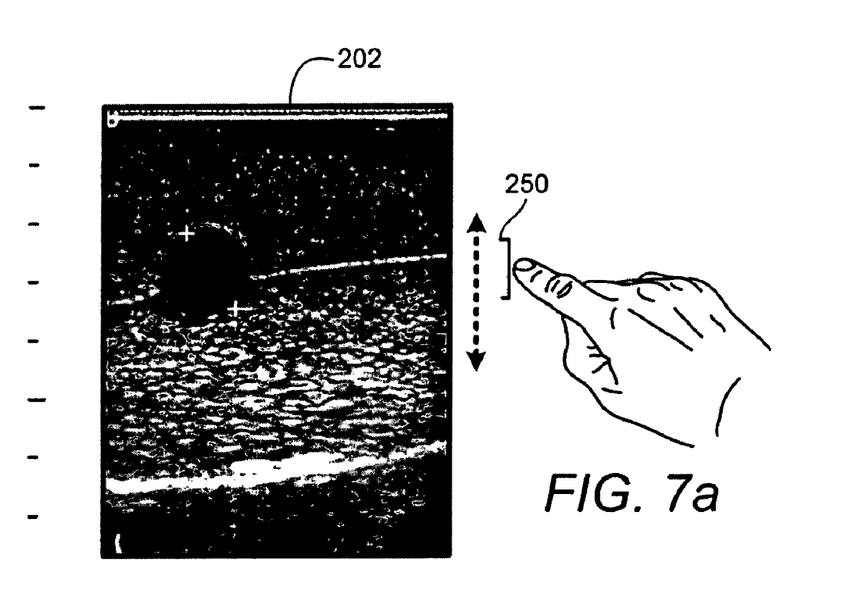
FIGS. 7a and 7b illustrate further detail of adjusting focal depth with a user interface, according to embodiments.
Figure 7B:
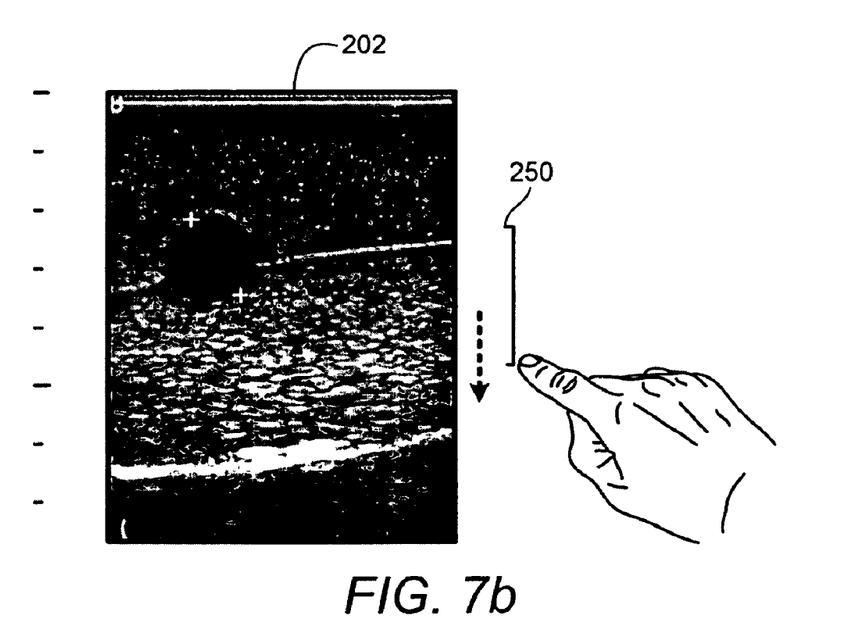

FIGS. 7a and 7b illustrate further detail of adjusting focal depth with a user interface, according to embodiments. In FIG. 7a, the focal depth indicator 250 indicates the focal depth range and position for the image being displayed in image area 202. The position of the focal depth can be adjusted by touching indicator 250 near the middle of the indicator, and dragging the indicator 250 to the new desired position. In response to the touch and drag operation the focal depth is adjusted and the corresponding images are displayed real time to the user. In FIG. 7b, the focal depth range is being adjusted by the user touching and dragging on either end of focal depth indicator 250. For example, if the user desires to increase the focal depth range on the lower end, the user touches the lower end of the indicator 250 and drags it to the new desired depth range limit.

Figure 8A:
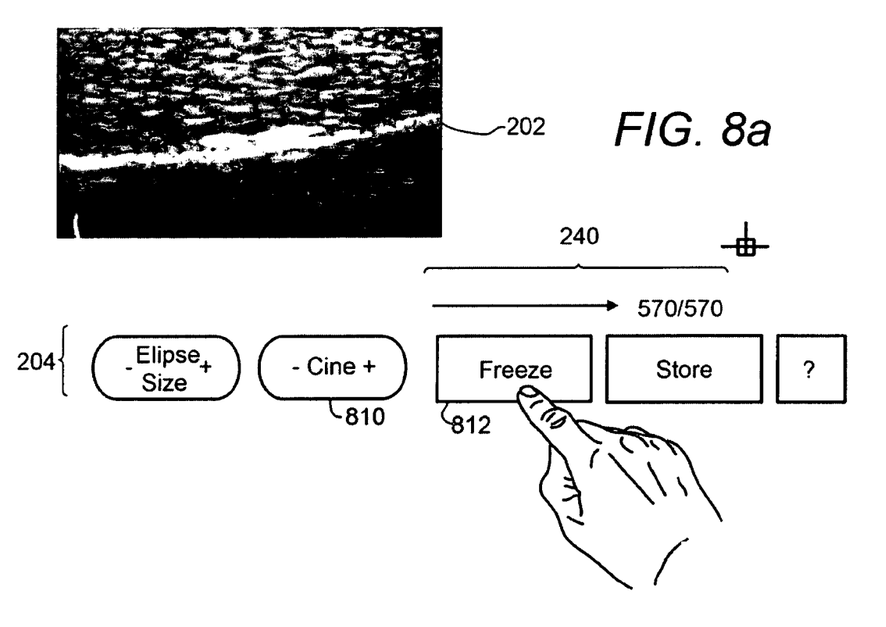
FIGS. 8a and 8b illustrate further detail of operating the cine loop functionality with a user interface, according to embodiments.
Figure 8B:
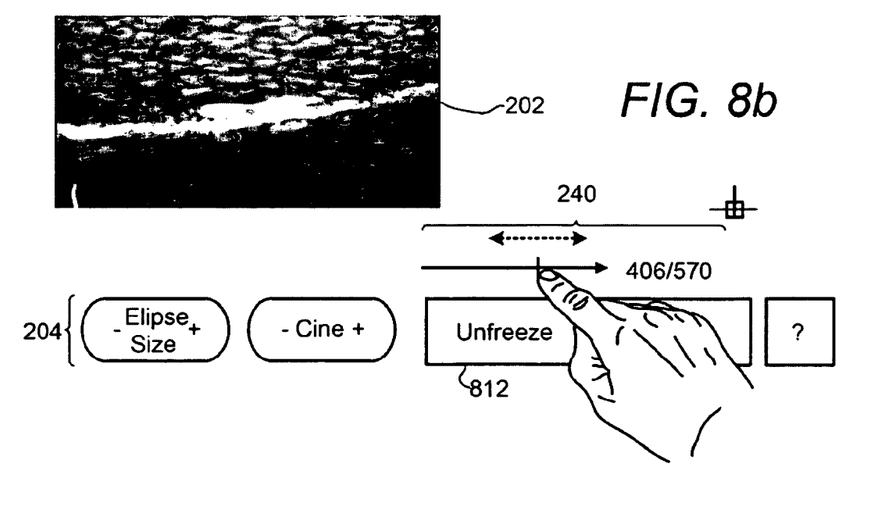

FIGS. 8a and 8b illustrate further detail of operating the cine loop functionality with a user interface, according to embodiments. In FIG. 8a, the live display of ultrasound images being displayed in image area 202 can be frozen by touching the freeze button 812 in menu area 204. After freezing the image, the stored frames can be redisplayed to the user by touching the Cine + or − symbols on cine control button 810 or using the cine slider in cine slider area 240. In the example shown in FIGS. 8a and 8b, 570 frames have been stored. In FIG. 8b, the cine playback is being controlled by touching and sliding the cross bar on the cine slider in cine slider area 240 in the left or right directions as shown by the broken arrow. Note that the when the image is frozen such that cine playback is activated, the button 812 toggles to an unfreeze button.

Figure 9:
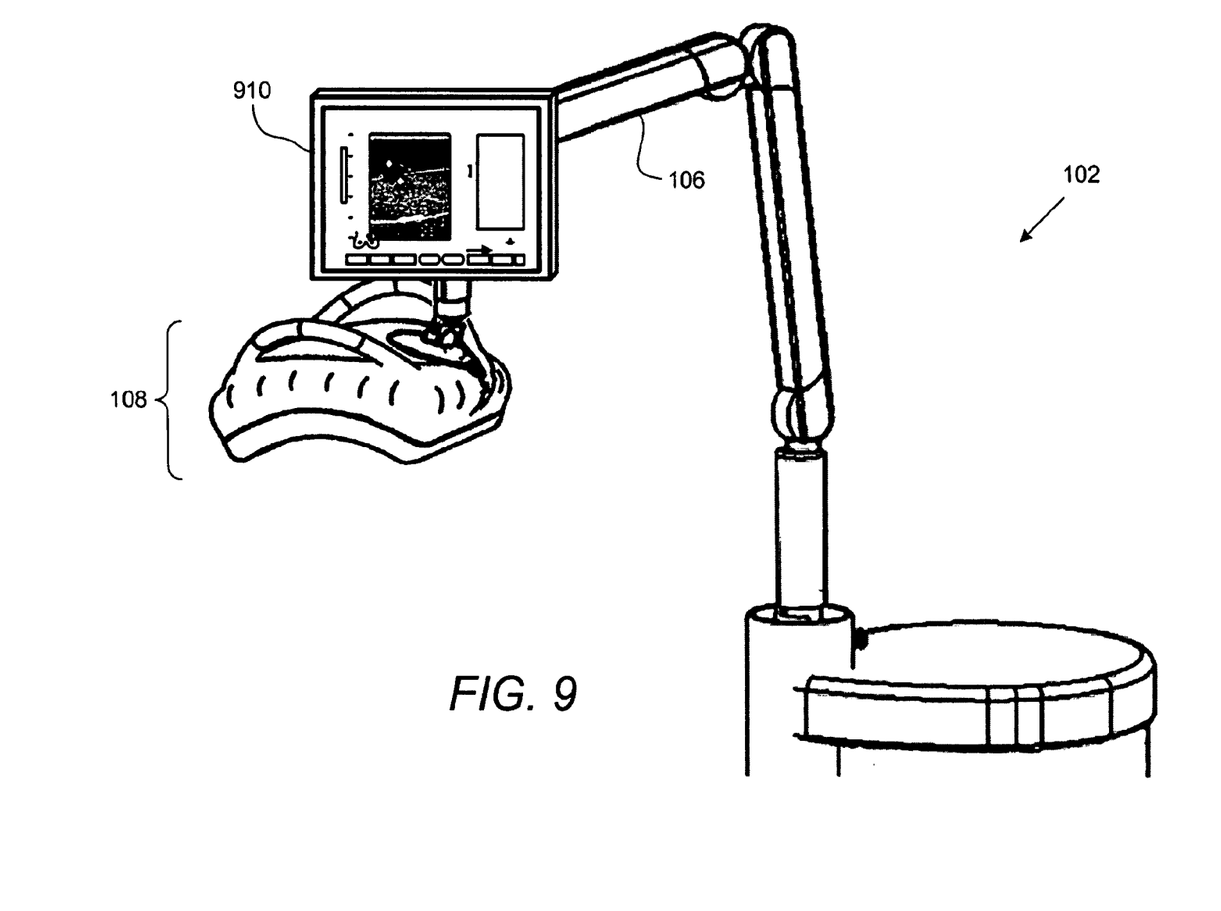
FIG. 9 shows a touchscreen user interface mounted in close proximity to a scanning pod, according to embodiments.

FIG. 9 shows a touchscreen user interface mounted in close proximity to a scanning pod, according to embodiments. Touchscreen user interface 910, which preferably can contain many or all of the user interface features described elsewhere herein, is mounted near the end of moveable support arm 106 such that the interface 910 is very near to the automated compression/scanning assembly 108. By placing the interface very close to the compression/scanning assembly 108, the user's attention is maintained in one general area, rather than being divided between several areas. In another embodiment, the touchscreen monitor is provided on a tablet PC having wireless (or, in another embodiment, wired) connectivity to rest of scanning apparatus 102. In yet another embodiment, the touchscreen user interface is provided on a tablet PC that is dockable to the apparatus 102 such as in a location near the end of arm 106.

Figure 10:
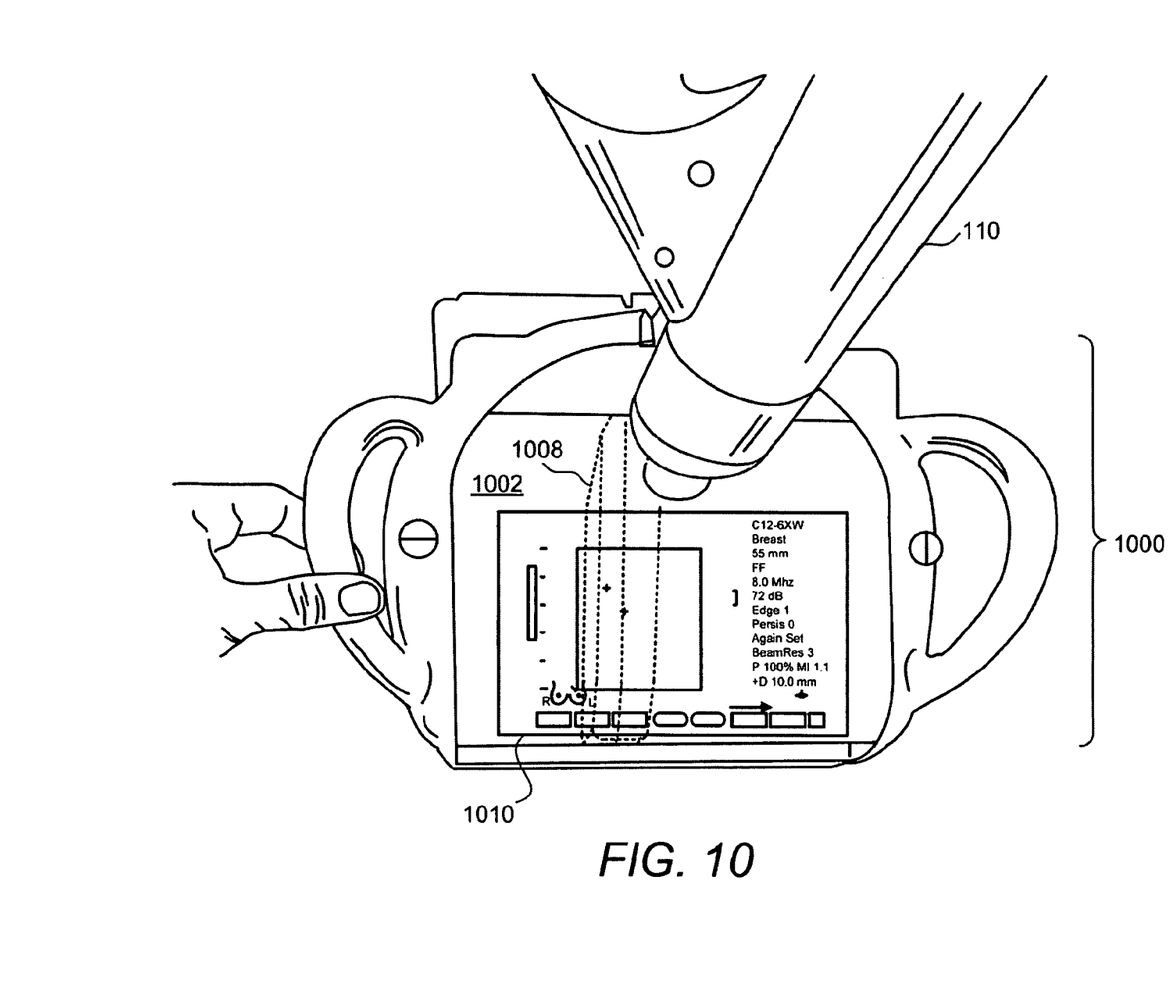
FIG. 10 shows a transparent touchscreen user interface mounted directly on a scanning pod, according to embodiments.

FIG. 10 shows a transparent touchscreen user interface mounted directly on a scanning pod, according to embodiments. Compression and scanning assembly 1000 is shown mounted on a ball-and-socket connector 110. The scanning assembly 1000 houses a ultrasound transducer 1008 that is swept across a lower membranous sheet that compresses the breast tissue. An upper panel 1002 of assembly 1000 is made transparent so as to facilitate proper placement of the assembly against the patent's breast tissue. Mounted directly on the transparent panel 1002 is a touch sensitive user interface 1010. Interface 1010 is preferably made of a transparent LCD material such that the transducer 1008, membrane and breast tissue below are still partly visible. Interface 1010 preferably contains many or all of the user interface features described elsewhere herein.

According to yet further embodiments, the touchscreen user interface functionalities described herein is also provided for thick-slice image viewing in systems such as described in International Patent Application No. WO2008/039389A1, and United States Published Patent Application Nos. US2005/0171430 and US2003/007598, each of which is incorporated herein by reference. When applied to thick-slice viewing, additional on-screen controls applicable to thick-slice viewing (e.g., slice thickness) can also be provided.

Whereas many alterations and modifications of the present invention will no doubt become apparent to a person of ordinary skill in the art after having read the foregoing description, it is to be understood that the particular embodiments shown and described by way of illustration are in no way intended to be considered limiting.

What is claimed is:

1. A system for acquiring and displaying ultrasound mammographic image information comprising:
   an ultrasound image acquisition device having at least one ultrasonic transducer positionable by a user on breast tissue of a patient so as to provide sonographic information of the breast tissue;
   a processing system for controlling the at least one ultrasonic transducer, receiving sonographic data from the transducer, and processing the data to generate sonographic image information for real time viewing by the user; and
   a graphical user interface including a touch-sensitive display programmed and configured to accept user adjustments with respect to the sonographic imaging process, and display the sonographic image information to the user responsive to the accepted adjustments in real time;
   wherein the ultrasound image acquisition device includes an automated breast compression and scanning assembly, and the graphical user interface is located on or close to the scanning assembly;
   and wherein the graphical user interface is mounted on the scanning assembly and is at least in part transparent so as to allow the user to view the underlying breast tissue during placement of the scanning assembly on the breast tissue.

2. A system according to claim 1 wherein the user adjustments are of one or more types selected from the group consisting of: depth of investigation, focal range, frequency, gain, edge enhancements, persistence, and beam resolution.

3. A system according to claim 1 wherein the ultrasound image acquisition device includes at least a first transducer unit and a second transducer unit, and wherein the adjustments include the capability for user to select between the first transducer unit and the second transducer unit.

4. A system according to claim 3 wherein the first transducer unit is a handheld transducer unit and the second transducer unit is an automated breast compression and scanning assembly.

5. A system according to claim 1 wherein the adjustments include automatic image enhancement.

6. A system according to claim 1 wherein the touch sensitive display is configured to accept user annotations with respect to the displayed sonographic image information and display the annotations in real time.

7. A system according to claim 1 wherein the touch sensitive display is configured to accept from the user digital caliper measurement locations using at least in part a touch and drag operation.

8. A system according to claim 1 wherein graphical user interface includes a conceptual outline of right and left breasts with a marker indicating the approximate location and orientation of the transducer.

9. A system according to claim 8 wherein the touch sensitive display is further programmed to accept from the user repositioning of the marker using at least in part a touch and drag operation.

10. A system according to claim 1 wherein the adjustments include the user adjusting the depth of investigation of the sonographic imaging process using at least in part a touch and drag operation in a depth ruler area.

11. A system according to claim 1 wherein the adjustments include the user adjusting the focal range position of the sonographic imaging process using at least in part a touch and drag operation on a displayed focal range maker.

12. A system according to claim 1 wherein the adjustments include the user adjusting the focal range size of the sonographic imaging processing using at least in part a touch and drag operation on a displayed focal range maker.

13. A system according to claim 1 wherein the touch-sensitive display is further programmed to accept user control over cine playback of sonographic image information using at least in part a touch and drag operation on a slider.

14. A method for acquiring and displaying ultrasound mammographic image information comprising:
    positioning an ultrasonic transducer unit on the breast tissue of a patient;
    acquiring sonographic information of the breast tissue from the transducer unit;
    processing the sonographic information for real time viewing by a user;
    accepting user adjustments with respect to the sonographic imaging process on a touch sensitive display; and
    displaying the processed sonographic information on the touch-sensitive display responsive to the accepted user adjustments;
    wherein the ultrasonic transducer unit forms part of an automated breast compression and scanning assembly, and the touch-sensitive display is located on or close to the scanning assembly;
    and wherein the touch-sensitive display is mounted on the scanning assembly and is at least in part transparent so as to allow the user to view the underlying breast tissue during positioning of the scanning assembly on the breast tissue.

15. A method according to claim 14 wherein the user adjustments are of one or more types selected from the group consisting of: depth of investigation, focal range, frequency, gain, edge enhancements, persistence, and beam resolution.

16. A method according to claim 14 wherein the adjustments include the capability for user to select between a first transducer unit and a second transducer unit.

17. A method according to claim 16 wherein the first transducer unit is a handheld transducer unit and the second transducer unit is an automated breast compression and scanning assembly.

18. A method according to claim 14 wherein the adjustments include automatic image enhancement.

19. A method according to claim 14 wherein the touch sensitive display is configured to accept user annotations with respect to the displayed sonographic image information and display the annotations in real time.

20. A method according to claim 14 wherein the touch sensitive display is configured to accept from the user digital caliper measurement locations using at least in part a touch and drag operation.

21. A method according to claim 14 wherein graphical user interface includes a conceptual outline of right and left breasts with a marker indicating the approximate location and orientation of the transducer unit with respect to the patient's breast tissue.

22. A method according to claim 21 further comprising repositioning the marker in response to a tap or touch and drag operation on the marker by the user.

23. A method according to claim 14 further comprising adjusting the depth of investigation of sonographic imaging in response to a tap or touch and drag operation in a depth ruler area by the user.

24. A method according to claim 14 further comprising adjusting the focal range position of the sonographic imaging in response to a touch and drag operation on a displayed focal range maker by the user.

25. A method according to claim 14 further comprising adjusting the focal range size of the sonographic imaging processing in response to a touch and drag operation on a displayed focal range maker by the user.

26. A method according to claim 14 further comprising playing back cine sonographic image information in response to a touch and drag operation on a slider by the user or a tap on a play marker next to the slider.

* * * * *